United States Patent [19]

Mita et al.

[11] 4,393,000

[45] Jul. 12, 1983

[54] CYCLIZATION PROCESS FOR PRODUCING AZIRIDINE-2-CARBOXYLIC ACID OR ITS SALTS

[75] Inventors: Ryuichi Mita, Kawasaki; Chojiro Higuchi, Kamakura; Toshio Kato, Kawasaki; Nobuyuki Kawashima; Akihiro Yamaguchi, both of Kamakura; Shosuke Nagai, Yokohama; Takao Takano, Fujisawa, all of Japan

[73] Assignee: Mitsui Toatsu Chemicals, Inc., Tokyo, Japan

[21] Appl. No.: 214,728

[22] Filed: Dec. 9, 1980

[30] Foreign Application Priority Data

Dec. 12, 1979 [JP] Japan ............................. 54/160351
Dec. 25, 1979 [JP] Japan ............................. 54/167681
Jan. 16, 1980 [JP] Japan ............................. 55/2566

[51] Int. Cl.³ ................ C07D 203/02; C07D 203/08
[52] U.S. Cl. .............................................. 260/239 E
[58] Field of Search ................................... 260/239 E

[56] References Cited

U.S. PATENT DOCUMENTS 3,336,294  8/1967  Miller ............................. 260/239 E
3,553,197  1/1971  Grenda ........................... 260/239 E
4,267,174  5/1981  Berger et al. ................... 260/239 E

OTHER PUBLICATIONS

Antonov et al., Z. Obshchei Khim 29, 1132, (1959).
Antonov et al., J. Gen. Chem. USSR, 39, 151–153, (1960).
Gundermann et al., *Chem. Ber.*, vol. 93, pp. 1632–1633 and 1638–1641, (1960).
Kyburz, E., *Hev. Chim. Acta*, vol. 49, pp. 359 and 368, (1966).

*Primary Examiner*—Mark L. Berch
*Attorney, Agent, or Firm*—Fisher, Christen & Sabol

[57] ABSTRACT

A process for producing aziridine-2-carboxylic acid or its salts is provided which comprises treating an alpha-halogeno-beta-aminopropionitrile or its mineral acid salt with an alkali or alkaline earth metal hydroxide in water or in a water-containing organic solvent. In a preferred embodiment, aziridine-2-carboxylic acid or its salt is produced by treating the reaction mixture containing an alpha-halogeno-beta-aminopropionitrile obtained by reacting an alpha, beta-dihalogenopropionitrile or an alpha-halogenoacrylonitrile with ammonia, with an alkali or alkaline earth metal hydroxide in the presence of water without isolating the alpha-halogeno-beta-aminopropionitrile from the reaction mixture beforehand.

13 Claims, No Drawings

CYCLIZATION PROCESS FOR PRODUCING AZIRIDINE-2-CARBOXYLIC ACID OR ITS SALTS

BACKGROUND OF THE INVENTION

This invention relates to a novel process for producing aziridine-2-carboxylic acid or its salt which is useful as an intermediate for the production of an alpha-amino acid, an agricultural chemical, a pharmaceutical, etc.

DESCRIPTION OF THE PRIOR ART

Some methods for the production of an aziridine-2-carboxylic acid salt have been known. For example, for the production of sodium aziridine-2-carboxylate, there are known (1) a method which comprises neutralizing alpha-chloro-beta-alanine hydrochloride in water with an aqueous solution of sodium hydroxide, and while heating the neutralization product under reflux, adding a 1 N aqueous solution of sodium hydroxide dropwise so that the pH of the aqueous solution is maintained at 7–7.5 [K. D. Gundermann, Chem. Ber., 93, 1640 (1960)], and (2) a method which comprises hydrolyzing isopropyl aziridine-2-carboxylate obtained by reaction between isopropyl alpha, beta-dibromopropionate and liquid ammonia, with sodium ethoxide in a mixed solvent consisting of ether, ethanol and water [E. Kyburz, Hev. Chim. Acta, 49, 368 (1966)]. Lithium aziridine-2-carboxylate is known to be produced by (3) a method which comprises treating alpha-chloro-beta-alanine, ethyl ester with triethanolamine in ethanol to form ethyl aziridine-2-carboxylate, and hydrolyzing the ethyl ester with lithium hydroxide in a mixed solvent consisting of ethanol and water [K. D. Gundermann, Chem. Ber., 93, 1639 (1960)]. The method (1), however, has the defect that it has to be operated while the concentration of the starting alpha-chloro-beta-alanine hydrochloride in the reaction system is maintained at as low as about 1% by weight. The methods (2) and (3), on the other hand, have the defect that synthesis of aziridine-2-carboxylic acid ester is complex and the yield of the final product is low. Accordingly, none of these prior methods are entirely satisfactory in commercial practice.

It is an object of this invention therefore to provide a commercially advantageous process for producing aziridine-2-carboxylic acid and its salts.

SUMMARY OF THE INVENTION

As a result of extensive investigations made in order to achieve the above object, we now provide a process which comprises treating a solution of an alpha-halogeno-beta-aminopropionitrile or its mineral acid salt in water or in a water-containing organic solvent with an alkali or alkaline earth metal hydroxide with optional heating. According to this process, hydrolysis of the nitrile group and intramolecular dehydrochlorination (cyclization) take place, and an alkali or alkaline earth metal salt of aziridine-2-carboxylic acid is formed almost selectively without substantially forming by-products.

We have also extensively investigated a commercially advantageous process for producing aziridine-2-carboxylic acid by using as a starting material an alpha-halogenoacrylonitrile which can be easily produced at low cost by halogenation and dehydrohalogenation of acrylonitrile or an alpha,beta-dihalogenopropionitrile which can be produced easily at low cost on a commercial scale by halogenation of acrylonitrile. As a result, we now provide a process for producing an aziridine-2-carboxylic acid salt which comprises reacting an alpha-halogenoacrylonitrile with ammonia in water and/or an organic solvent to form an alpha-halogeno-beta-aminopropionitrile, adding an alkali or alkaline earth metal hydroxide in the form of an aqueous solution, an aqueous suspension or a solid to the resulting reaction mixture without isolating the product therefrom, and if desired, heating the mixture; and a process for producing an aziridine-2-carboxylic acid which comprises reacting an alpha,beta-dihalogenopropionitrile with ammonia in water and/or an organic solvent to form an alpha-halogeno-beta-aminopropionitrile, adding an alkali or alkaline earth metal hydroxide in the form of an aqueous solution, an aqueous suspension or a solid to the resulting reaction mixture without isolating the product therefrom, and if desired, heating the mixture.

The processes of this invention have various advantages over the aforesaid known methods in that the starting materials can be produced easily at low cost, the reaction operation is simple, the process steps are markedly simplified, and the desired aziridine-2-carboxylic acid can be obtained in a high yield. Accordingly, they are of high utilitarian value in commercial practice.

DETAILED DESCRIPTION OF THE INVENTION

The alpha-halogeno-beta-aminopropionitrile or its mineral acid salt used in the processes of this invention includes, for example, alpha-chloro-beta-aminopropionitrile, alpha-bromo-beta-aminopropionitrile, alpha-chloro-beta-aminopropionitrile hydrochloride and sulfate, and alpha-bromo-beta-aminopropionitrile hydrochloride and sulfate.

The alpha-halogeno-beta-aminopropionitrile or its mineral acid salt is obtained by reacting an alpha,beta-dihalogeno-propionitrile or an alpha-halogenoacrylonitrile with ammonia in water or an organic solvent. A free alpha-halogeno-beta-aminopropionitrile is obtained by distilling under reduced pressure the reaction mixture or the extract obtained by extracting the reaction product from the reaction mixture with a water-immiscible organic solvent. Action of hydrochloric acid or sulfate on the reaction mixture gives an alpha-halogeno-beta-aminopropionitrile hydrochloride or sulfate. For example, alpha-chloro-beta-aminopropionitrile hydrochloride can be isolated in a yield of more than 80% by adding dropwise alpha-chloroacrylonitrile at about 0° C. to a solution of ammonia as in isopropanol, reacting them at this temperature for 2 to 4 hours, and feeding a solution of hydrogen chloride in isopropanol.

The aqueous solution or water-containing organic solvent solution containing the alpha-halogeno-beta-aminopropionitrile or its mineral acid salt used in the processes of this invention may be a reaction mixture containing an alpha-halogeno-beta-aminopropionitrile obtained by the reaction of (1) an alpha, beta-dihalogenopropionitrile or (2) an alpha-halogenoacrylonitrile with ammonia. This reaction mixture is described more specifically below.

(1) First, there will be described the reaction mixture containing an alpha-halogeno-beta-aminopropionitrile obtained by reacting an alpha,beta-dihalogenopropionitrile with ammonia in water and/or an organic solvent.

The starting alpha,beta-dihalogenopropionitrile may be any of chlorine, bromine, iodine and fluorine derivatives, but alpha,beta-dichloropropionitrile and alpha,- beta-dibromopropionitrile are preferred. The alpha,-beta-dihalogenopropionitrile can be easily produced by halogenation of acrylonitrile.

Ammonia used in the production of the alpha-halogeno-beta-aminopropionitrile is used in the form of aqueous ammonia or a solution of ammonia gas or aqueous ammonia in an organic solvent. The reaction may also be performed while introducing ammonia gas into the reaction system. The organic solvent used in the reaction denotes an organic solvent having the ability to dissolve ammonia. Generally, it is a lower alcohol such as methanol, ethanol, n-propanol, isopropanol, n-butanol, isobutanol, tert.-butanol, methyl Cellosolve or Cellosolve. Two or more of these organic solvents may be used in combination. Such an organic solvent may also be used as a mixture with water.

The amounts of the alpha,beta-dihalogenopropionitrile and ammonia are such that at least 2 moles, preferably at least 2.2 moles, of ammonia is used per mole of the alpha,beta-dihalogenopropionitrile. When the reaction is carried out in aqueous ammonia, ammonia is used as a 5–30% by weight solution. When the reaction is carried out in an organic solvent or a water-containing organic solvent, ammonia is used as a solution having a concentration of 2 to 25% by weight.

In the reaction of forming the alpha-halogeno-beta-aminopropionitrile, there is no particular limitation on the method and order of adding the starting material and the solvent, etc. Usually, it is preferred to add the alpha,beta-dihalogenopropionitrile gradually to water and/or an organic solvent containing water. The alpha,-beta-dihalogenopropionitrile may be added after it is diluted with an organic solvent.

The reaction temperature is −40° to 30° C., preferably −20° to 20° C., and the reaction time is 0.5 to 20 hours, preferably 1 to 15 hours. The reaction may be performed in an atmosphere of air. Preferably, it is carried out in an inert gas, for example in a nitrogen atmosphere or nitrogen stream, because side-reactions can be inhibited in the inert gas.

The end point of the reaction between the alpha,beta-dihalogenopropionitrile and ammonia can be rapidly and easily determined by gas chromatography, high-speed liquid chromatography, etc.

(2) The reaction mixture containing an alpha-halogeno-beta-aminopropionitrile obtained by reacting an alpha-halogenoacrylonitrile with ammonia in water and/or an organic solvent is described below specifically.

Usually, alpha-chloroacrylonitrile and alpha-bromoacrylonitrile are frequently used as the alpha-halogenoacrylonitrile.

Ammonia is used in the form of aqueous ammonia or a solution of ammonia gas or aqueous ammonia in an organic solvent. The reaction between the alpha-halogenoacrylonitrile and ammonia may be carried out in water and/or an organic solvent. When the reaction is carried out in an organic solvent, the organic solvent used is a compound having the ability to dissolve ammonia. Suitable organic solvents are lower alcohols such as methanol, ethanol, n-propanol, isopropanol, n-butanol, isobutanol, tert.-butanol, methyl Cellosolve and Cellosolve. They are used either singly or as a mixture of two or more. These organic solvents may be used as a mixture with water.

The amounts of the alpha-halogenoacrylonitrile and ammonia are such that at least 1 mole, preferably at least 1.2 moles, of ammonia is used per mole of the alpha-halogenoacrylonitrile. When the reaction is carried out in aqueous ammonia, ammonia is used as a solution having a concentration of 5 to 30% by weight. When the reaction is carried out in an organic solvent or a water-containing organic solvent, ammonia is used as a solution having a concentration of 2 to 25% by weight.

In the reaction of the alpha-halogenoacrylonitrile with ammonia, there is no particular limitation on the method and order of adding the starting material and the solvent. Usually, it is preferred to add the alpha-halogenoacrylonitrile to water and/or an organic solvent containing ammonia. The alpha-halogenoacrylonitrile may be added after it is diluted with an organic solvent.

The reaction temperature is −40° to 30° C., preferably −20° to 20° C., and the reaction time is 0.5 to 20 hours, preferably 1 to 15 hours. The reaction may be carried out in an atmosphere of air or an inert gas. The use of an inert gaseous atmosphere, for example a nitrogen atmosphere or nitrogen stream, is preferred since side-reactions can be inhibited in the inert gaseous atmosphere. The end point of the reaction can be easily and rapidly determined by gas chromatography, high-speed liquid chromatography, etc.

The alkali or alkaline earth metal hydroxide used in this invention includes hydroxides of alkali metals such as lithium, sodium, potassium and rubidium, and hydroxides of alkaline earth metals such as beryllium, magnesium, calcium, strontium and barium. Specific examples are lithium hydroxide, sodium hydroxide, potassium hydroxide, beryllium hydroxide, magnesium hydroxide, calcium hydroxide and barium hydroxide. Usually, sodium hydroxide, potassium hydroxide and calcium hydroxide are preferred.

In the processes of this invention, the amount of the alkali or alkaline earth metal hydroxide is at least 2 equivalents based on the starting material when it is a free alpha-halogeno-beta-aminopropionitrile, and at least 3 equivalents based on the starting material when it is a mineral acid salt of an alpha-halogeno-beta-aminopropionitrile. There is no particular upper limit to the amount of the hydroxide. But it is not necessary to use it in large excess, and usually up to 5 equivalents are sufficient.

When the reaction mixture from the alpha,beta-dihalogenopropionitrile or alpha-halogenoacrylonitrile is subsequently treated with alkalies, the amount of the alkali or alkaline earth metal used is at least 2 equivalents, preferably at least 2.2 equivalents, based on the alpha,beta-dihalogenopropionitrile or alpha-halogenoacrylonitrile. There is no particular limitation to the upper limit of the amount of the alkali or alkaline earth metal. But it is not necessary to use it in large excess, and usually, up to 5 equivalents are sufficient.

The processes of this invention are carried out in water or in a water-containing organic solvent. In other words, the reaction is carried out in an aqueous solution, or in a mixture of water and a water-miscible organic solvent.

Examples of the water-miscible organic solvent are methanol, ethanol, n-propanol, isopropanol, tert-butanol, Cellosolve, methyl Cellosolve, acetone, dioxane, tetrahydrofuran, N,N-dimethyl formamide, N,N-diethyl formamide and dimethyl sulfoxide. When water and the organic solvent are used in combination, the ratio of water to the organic solvent may be chosen as desired. the amount of the solvent used is 3 to 200 times, preferably 5 to 100 times, the amount of the starting alpha-halogeno-beta-aminopropionitrile or its mineral acid salt.

In performing the processes of this invention, there is no limitation on the method and order of adding the starting material, the alkali and the reaction solvent. Usually, a predetermined amount of the alkali or alkaline earth metal hydroxide in the form of an aqueous solution or suspension is added to a solution of the alpha-halogeno-beta-aminopropionitrile or its mineral acid salt in water and/or a water-miscible organic solvent in a desired concentration. Or conversely, the solution containing the alpha-halogeno-beta-aminopropionitrile may be added to the aqueous solution or suspension of the alkali or alkaline earth metal hydroxide. When the reaction mixture containing an alpha-halogeno-beta-aminopropionitrile derived from an alpha,beta-dihalogenopropionitrile or an alpha-halogenoacrylonitrile is used, it is possible, if desired, to treat a solution of the reaction mixture in water and/or the organic solvent with the hydroxide in the same manner as above.

The alkali or alkaline earth metal hydroxide may be added as a solid.

When by-product ammonium chloride precipitates from the reaction mixture containing an alpha-halogeno-beta-aminopropionitrile, the reaction mixture is submitted to hydrolysis after separating the ammonium chloride from it. When the reaction of forming the alpha-halogeno-beta-aminopropionitrile is carried out in an organic solvent, water should be added for the subsequent hydrolysis and cyclization reaction. The amount of water to be added is not particularly limited, and the ratio between the organic solvent and water can be chosen as desired.

The reaction temperature is 0° to 100° C., preferably 20° to 80° C. The reaction is carried out usually at atmospheric pressure, but if desired, it may be performed under reduced or elevated pressure. The reaction time varies depending upon the various reaction conditions, but is usually 0.5 to 50 hours, particularly 2.0 to 30 hours. The end point of the reaction can be easily and rapidly determined by thin-layer chromatography.

In the processes of this invention, aziridine-2-carboxylic acid is formed as an alkali metal salt or an alkaline earth metal salt corresponding to the alkali used in the reaction. If desired, the organic solvent may be removed under reduced pressure from the product to obtain the product in the form of an aqueous solution.

The following Examples illustrate the processes of this invention more specifically.

Lithium aziridine-2-carboxylate as a standard sample used in the Examples was synthesized in the following manner. Analysis by high-speed liquid chromatography was performed under the following conditions.

(a) Production of lithium aziridine-2-carboxylate 10 g of ethyl alpha-chloro-beta-aminopropionate hydrochloride was dissolved in 100 ml of dehydrated ethanol, and 20 g of triethanolamine was added. With stirring, they were reacted at 60° to 70° C. for 5 hours. The precipitated triethanolamine hydrochloride was separated by filtration, and washed with a small amount of ethanol. The filtrate and the washing were combined, and with cooling, 55 ml of a 1 N aqueous solution of lithium hydroxide was gradually added. The mixture was allowed to stand for 24 hours in a cold dark place. The reaction mixture was then concentrated to dryness under reduced pressure. Then, 30 ml of benzene was added to the residue (syrupy material), and water was completely removed by azeotropic distillation. Then, 50 ml of hot ethanol was added, and the mixture was cooled to form a precipitate. 100 ml of ether was added to precipitate the crystals fully. The precipitate was separated by filtration, and washed with ether to afford 1.0 g of lithium aziridine-2-carboxylate.

Melting point: 260°–268° C. (decomp.)

| Elemental analysis (%) for $C_3H_4NO_2Li$: | | | | |
|---|---|---|---|---|
|  | C | H | N | Li |
| Found (%): | 37.86 | 4.23 | 14.71 | 7.40 |
| Calculated (%): | 38.74 | 4.33 | 15.06 | 7.46 |

The purity of the resulting lithium aziridine-2-carboxylate, determined by proton NMR spectroscopy using dioxane as an internal standard (measuring solvent: $D_2O$, measuring temperature: room temperature), was 97%.

(b) Conditions for analysis by high-speed liquid chromatography

Column: Shodex OH Pak B-804 (a product of Showa Denko Co., Ltd.)

Detector: Differential refractometer RI-2 (a product of Nippon Bunseki Kogyo Co., Ltd.)

Mobile phase: Aqueous solution of $H_3PO_4$ ($1 \times 10^{-3}$ mole/liter)

Flow rate: 1.3 ml/min.

Measuring temperature: room temperature

Under these conditions, the retention time of aziridine-2-carboxylic acid was 16.5 to 16.8 minutes.

EXAMPLE 1

28.2 g of alpha-chloro-beta-aminopropionitrile hydrochloride was dissolved in 80 g of water. Then, with stirring, an aqueous solution of 25.6 g of sodium hydroxide in 84 g of water was added dropwise, and they were reacted at room temperature for 24 hours. The reaction mixture was analyzed by high-speed liquid chromatography using lithium arizidine-2-carboxylate as a standard sample. The yield of sodium aziridine-2-carboxylate formed was 95.5% based on the alpha-chloro-beta-aminopropionitrile hydrochloride.

When the resulting reaction mixture was analyzed by proton NMR spectroscopy, a signal attributed to the methylene proton of aziridine-2-carboxylic acid was detected at $\delta = 1.79$ ppm (q., 2H), and a signal attributed to the methine protone, at $\delta = 2.35$ ppm (q., 1H). This signal pattern was identical with that of lithium aziridine-2-carboxylate synthesized as a standard sample.

EXAMPLE 2

14.1 g of alpha-chloro-beta-aminopropionitrile hydrochloride was dissolved in 160 g of water. With stirring, an aqueous solution of 22.4 g of potassium hydroxide in 90 g of water was added dropwise. Then, the reaction mixture was heated to 60° C., and reacted at 60° to 65° C. for 4 hours. The reaction mixture was analyzed by high-speed liquid chromatography in the same way as in Example 1. The yield of potassium aziridine-2-carboxylate formed was 92.3%.

EXAMPLE 3

Example 2 was repeated except that 10.5 g of free alpha-chloro-beta-aminopropionitrile was used instead of the alpha-chloro-beta-aminopropionitrile hydrochloride in Example 2, and 13 g of lithium hydroxide was used instead of potassium hydroxide. The yield of lithium aziridine-2-carboxylate formed was 90.8%.

EXAMPLE 4

Example 2 was repeated except that 15.3 g of alpha-chloro-beta-aminopropionitrile sulfate was used instead of the alpha-chloro-beta-aminopropionitrile hydrochloride in Example 2. The yield of lithium aziridine-2-carboxylate formed was 94.2%.

EXAMPLE 5

14.1 g of alpha-chloro-beta-aminopropionitrile hydrochloride was dissolved in 160 g of water, and with stirring, 12 g of calcium hydroxide was gradually added. Then, the reaction mixture was heated to 60° C., and reacted at 60° to 65° C. for 8 hours. After the reaction, the excess of calcium hydroxide was removed by filtration. The residue was analyzed by high-speed liquid chromatography in the same way as in Example 1. The yield of calcium aziridine-2-carboxylate formed was 92.5%.

EXAMPLE 6

14.1 g of alpha-chloro-beta-aminopropionitrile hydrochloride was dissolved in 150 g of methanol, and with stirring an aqueous solution of 12.8 g of sodium hydroxide in 75 g of water was added dropwise. Then, the reaction mixture was heated to 60° C., and reacted at this temperature for 10 hours. Thereafter, the methanol in the reaction mixture was distilled off under reduced pressure, and the residue was analyzed by high-speed liquid chromatography. The yield of sodium aziridine-2-carboxylate formed was 89.2%.

EXAMPLE 7

Example 6 was repeated except that 150 g of isopropanol was used instead of the methanol. The yield of sodium aziridine-2-carboxylate formed with 93.5%.

EXAMPLE 8

60.8 g of conc. aqueous ammonia (concentration 28% by weight) was maintained at 0° C., and with stirring in a gentle stream of nitrogen, 24.8 g of alpha,beta-dichloropropionitrile was added dropwise over the course of about 2 hours. The reaction was performed further for 3 hours at 0° to 5° C. Then, an aqueous solution of 25.6 g of sodium hydroxide in 150 g of water was added dropwise over the course of about 30 minutes, and the reaction was performed further at room temperature for 30 hours. The reaction mixture was analyzed by high-speed liquid chromatography. The yield of sodium aziridine-2-carboxylate formed was 80.1% based on the alpha,beta-dichloropionitrile. The retention time was 16.5 minutes.

In a proton NMR spectrum of the reaction mixture (measuring temperature: room temperature), signals were observed only at $\delta = 1.79$ ppm (q., 2H) and $\delta = 2.35$ ppm (q., 1H). These signals were identical with those of the lithium aziridine-2-carboxylate as a standard sample in aqueous solution.

EXAMPLE 9

225 g of an isopropanol solution having dissolved therein ammonia gas in a concentration of 6.8% by weight was maintained at 0° C., and in a gentle stream of nitrogen, 24.8 g of alpha,beta-dichloropropionitrile was added dropwise over the course of about 2 hours with stirring. Then, the reaction was performed at 0° to 5° C. for 3 hours to form alpha-chloro-beta-aminopropionitrile. Then, while the reaction mixture was externally cooled, an aqueous solution of 25.6 g of sodium hydroxide in 230 g of water was gradually added dropwise. The solution was then heated to 50° C., and reacted at 50° to 55° C. for 7 hours. Isopropanol was distilled off from the reaction mixture under reduced pressure, and the residue was analyzed by high-speed liquid chromatography in the same way as in Example 8. The yield of sodium aziridine-2-carboxylate formed was 90.8% based on the alpha,beta-dichloropropionitrile.

EXAMPLES 10 TO 13

Example 9 was repeated except that each of the alkalies shown in Table 1 was used instead of sodium hydroxide. An aqueous solution of an alkali or alkaline earth metal aziridine-2-carboxylate corresponding to the used alkali was obtained. The yield of the final product formed was as shown in Table 1.

TABLE 1

| | Alkali used | | Yield of the aziridine-2-carboxylate based on alpha,beta-dichloropropionitrile (%) |
|---|---|---|---|
| Example | Type | Amount (g) | |
| 10 | Lithium hydroxide | 25.2 | 91.5 |
| 11 | Potassium hydroxide | 35.9 | 89.7 |
| 12 | Calcium hydroxide | 23.7 | 89.4 |
| 13 | Magnesium hydroxide | 18.7 | 88.6 |

EXAMPLES 14 TO 16

Example 9 was repeated except that, each of the solvents shown in Table 2 was used instead of isopropanol. The yield of the resulting sodium aziridine-2-carboxylate is shown in Table 2.

TABLE 2

| Example | Solvent | Yield of sodium aziridine-2-carboxylate based on alpha,beta-dichloropropionitrile (%) |
|---|---|---|
| 14 | Methanol | 86.3 |
| 15 | Ethanol | 90.4 |
| 16 | Methyl cellosolve | 87.6 |

EXAMPLE 17

Example 9 was repeated except that the reaction between alpha,beta-dichloropropionitrile and ammonia was carried out at 15° to 20° C. An aqueous solution of sodium aziridine-2-carboxylate was obtained in a yield of 91.3 mole % based on the alpha,beta-dichloropropionitrile.

EXAMPLE 18

A solution obtained by dissolving 17 g of ammonia gas in 200 g of hydrous ethanol containing 20% by weight of water was cooled to 0° C., and in a gentle stream of nitrogen, 24.8 g of alpha,beta-dichloropropionitrile was added dropwise over the course of about 2 hours with stirring. The reaction was performed further at 0° to 5° C. for 4 hours to form alpha-chloro-beta-aminopropionitrile. Then, the reaction mixture was added dropwise to an aqueous solution of 25.6 g of sodium hydroxide in 200 g of water with external cooling. The solution was then heated to 60° C., and reacted at 60° to 65° C. for 5 hours. Ethanol was distilled off from the reaction mixture under reduced pressure, and the residue was analyzed by high-speed liquid chromatography in the same way as in Example 1. The yield of sodium aziridine-2-carboxylate formed was 86.7% based on the alpha,beta-dichloropropionitrile.

EXAMPLE 19

60.8 g of conc. aqueous ammonia (concentration 28%) was maintained at 0° C., and with stirring in a gentle stream of nitrogen, 17.5 g of alpha-chloroacrylonitrile was added dropwise over the course of about 2 hours. Then, the reaction was performed at 0° to 50° C. for 4 hours. An aqueous solution of 17.6 g of sodium hydroxide in 120 g of water was added dropwise over the course of about 30 minutes, and the reaction was performed further at room temperature for 30 hours. The reaction mixture was analyzed by high-speed liquid chromatography. The yield of sodium aziridine-2-carboxylate formed was 78.6% based on the alpha-chloroacrylonitrile.

In a proton NMR spectrum (measuring temperature: room temperature) of the reaction mixture, signals were oberved only at $\delta=1.79$ ppm (q., 2H) and $\delta=2.35$ ppm (q., 1H). These signals were identical with those of lithium aziridine-2-carboxylate as a standard sample in aqueous solution.

EXAMPLE 20

200 g of an isopropanol solution having dissolved therein ammonia gas in a concentration of 6.8% by weight was maintained at 0° C., and in a gentle stream of nitrogen, 17.5 g of alpha-chloroacrylonitrile was gradually added dropwise over the course of about 1.5 hours with stirring. Thereafter, the reaction was performed at 0° to 5° C. for 2 hours to form alpha-chloro-beta-aminopropionitrile. Then, while the reaction mixture was cooled externally, a solution of 17.6 g of sodium hydroxide in 200 g of water was gradually added dropwise. The solution was heated to 50° C., and reacted at 50° to 60° C. for 8 hours. Isopropanol was distilled off from the reaction mixture under reduced pressure, and the residue was analyzed by high-speed liquid chromatography. The yield of sodium aziridine-2-carboxylate formed was 88% based on the alpha-chloroacrylonitrile.

EXAMPLES 21 TO 23

Example 20 was repeated except that each of the alkalies shown in Table 3 was used instead of sodium hydroxide. An aqueous solution of the corresponding alkali or alkaline earth metal salt of aziridine-2-carboxylic acid was obtained in the yields shown in Table 3.

TABLE 3

| Example | Alkali used Type | Amount (g) | Yield of the aziridine-2-carboxylate salt based on alpha-chloro-acrylonitrile (%) |
| --- | --- | --- | --- |
| 21 | Lithium hydroxide | 18.5 | 87.5 |
| 22 | Potassium hydroxide | 25.0 | 89.6 |
| 23 | Calcium hydroxide | 16.3 | 90.1 |

TABLE 3-continued

| Example | Alkali used Type | Amount (g) | Yield of the aziridine-2-carboxylate salt based on alpha-chloro-acrylonitrile (%) |
| --- | --- | --- | --- |
| | hydroxide | | |

EXAMPLE 24

Example 20 was repeated except that methanol was used instead of isopropanol. An aqueous solution of sodium aziridine-2-carboxylate was obtained in a yield of 85.1%.

EXAMPLE 25

Example 20 was repeated except that the reaction between alpha-chloroacrylonitrile and ammonia was carried out at 15° to 20° C. An aqueous solution of sodium aziridine-2-carboxylate was obtained in a yield of 90.4%.

What is claimed is:

1. A process for producing aziridine-2-carboxylic acid salt which comprises a step wherein an α-halogeno-β-aminopropionitrile-containing reaction mixture obtained by reacting an α,β-dihalogenopropionitrile or an α-halogenoacrylonitrile with ammonia in water, an organic solvent or a mixture of water and an organic solvent at a temperature of −40° to 30° C., is treated with an alkali or alkaline earth metal hydroxide.

2. The process of claim 1 wherein the ammonia is used in water in a concentration of 5 to 30% by weight, or in an organic solvent or a water-containing organic solvent in a concentration of 2 to 25% by weight.

3. The process of claim 1 wherein the alpha-halogeno-beta-aminopropionitrile-containing reaction mixture is obtained by reacting an alpha-halogenoacrylonitrile with ammonia in water and/or an organic solvent.

4. The process of claim 1 wherein the alpha-halogeno-beta-aminopropionitrile-containing reaction mixture is obtained by reacting an alpha,beta-dihalogenopropionitrile with ammonia in water and/or an organic solvent.

5. The process of claim 3 wherein the α-halogenoacrylonitrile is an α-chloroacrylonitrile or an α-bromoacrylonitrile.

6. The process of claim 4 wherein the α,β-dihalogenopropionitrile is an α,β-dichloropropionitrile or α,β-dibromopropionitrile.

7. The process of claim 1 wherein the alkali or alkaline earth metal hydroxide is sodium hydroxide, potassium hydroxide or calcium hydroxide.

8. The process of claim 1 wherein the organic solvent is a compound which dissolves ammonia.

9. The process of claim 8 wherein the compound which dissolves ammonia is methanol, ethanol, propanol, isopropanol, n-butanol, isobutanol, methyl Cellosolve or Cellosolve.

10. The process of claim 3 wherein at least 1 mole of ammonia per mole of the α-halogenoacrylonitrile is reacted.

11. The process of claim 4 wherein at least 2 moles of ammonia per mole of the α,β-dihalogenopropionitrile is reacted.

12. The process of claim 3 wherein the amount of the alkali or alkaline earth metal hydroxide is at least 2 equivalents based on the α-halogenoacrylonitrile.

13. The process of claim 4 wherein the amount of the alkali or alkaline earth metal hydroxide is at least 2 equivalents based on the α,β-dihalogenopropionitrile.

* * * * *